United States Patent [19]

Ramachandran et al.

[11] Patent Number: 5,488,185
[45] Date of Patent: Jan. 30, 1996

[54] PROCESS FOR THE PRODUCTION OF ETHANOL AND ISOPROPANOL

[75] Inventors: Ramakrishnan Ramachandran, Allendale; Loc H. Dao, Bound Brook, both of N.J.

[73] Assignee: The BOC Group, Inc., New Providence, N.J.

[21] Appl. No.: 231,560

[22] Filed: Apr. 22, 1994

Related U.S. Application Data

[63] Continuation-in-part of Ser. No. 129,637, Sep. 30, 1993, abandoned.

[51] Int. Cl.⁶ .......................... C07C 29/04; C07C 31/08; C07C 31/10; C07C 7/12
[52] U.S. Cl. .......................... 568/896; 568/895; 568/897; 568/898; 568/899; 568/900; 568/901; 585/829
[58] Field of Search .................................. 568/895–901; 585/829

[56] References Cited

U.S. PATENT DOCUMENTS

| | | | |
|---|---|---|---|
| 2,050,442 | 8/1936 | Metzger | 568/899 |
| 2,052,806 | 9/1936 | Shiffler et al. | 568/899 |
| 2,228,027 | 1/1941 | Bent et al. | 568/899 |
| 2,992,189 | 7/1961 | Friedman et al. | 568/899 |
| 3,994,983 | 11/1976 | Weber et al. | 568/899 |
| 4,306,101 | 12/1981 | Slaugh et al. | 568/899 |
| 4,456,776 | 6/1984 | Neier et al. | 568/899 |
| 4,917,711 | 4/1990 | Xie et al. | 55/68 |
| 5,365,011 | 11/1994 | Ramschandran | 585/829 |

FOREIGN PATENT DOCUMENTS 221128  5/1980  German Dem. Rep. .

OTHER PUBLICATIONS

Adsorptive Separation of Propylene–Propane Mixtures–Harri Jarvelin and James R. Fair (1993) Ind. Eng. Chem. Res., vol. 32, No. 10 (1993) pp. 2201–2207.
Zeolite Molecular Sieves–Donald W. Breck–Union Carbide Corporation (1974) pp. 635–642.

*Primary Examiner*—Joseph E. Evans
*Attorney, Agent, or Firm*—Coleman R. Reap; Larry R. Cassett

[57] ABSTRACT

An ethene stream which contains ethane as an impurity or a propene stream which contains propane as an impurity is hydrated with water vapor in the presence of a hydration catalyst to produce ethanol or isopropanol, respectively. After removal of the alcohol the gaseous product stream is subjected to adsorption, thereby producing an ethene-enriched stream or a propene-enriched stream. The ethene-enriched stream or the propene-enriched stream is recycled to the hydration reactor.

15 Claims, 1 Drawing Sheet

PROCESS FOR THE PRODUCTION OF ETHANOL AND ISOPROPANOL

RELATED CASE

This application is a continuation-in-part of application Ser. No. 129,637, filed Sep. 30, 1993, now abandoned.

FIELD OF THE INVENTION

The present invention is directed to a process for producing alcohols by the direct hydration of alkenes, and more particularly to a process in which ethanol or isopropanol is produced by contacting an ethene stream containing ethane as an impurity or a propene stream containing propane as an impurity with water in the presence of an appropriate hydration catalyst.

BACKGROUND OF THE INVENTION

Ethanol and isopropanol are produced commercially by the direct hydration of ethene or propene, respectively, in the liquid or vapor phase over a suitable catalyst. The reaction can be carried out in any suitable reactor and it produces the desired alcohol product and generally small amounts of byproducts, such as diethyl ether, in the case of ethanol production and diisopropyl ether, in the case of isopropanol production. The reaction conversion is usually less than 100%; accordingly the reactor effluent also generally contains unreacted ethene or propene. Furthermore, chemical grade ethene and propene usually contains small amounts of ethane and/or propane. Therefore, since ethane and propane are not generally affected by ethene and propene direct hydration catalysts, the reactor effluent contains ethane and/or propane.

To enhance selectivity to the desired product the hydration reaction is generally carried out at a hydrocarbon conversion per pass somewhat lower than 100% (as low as 5% for ethene hydration and generally about 60 to 75% for propene hydration). Accordingly, to improve efficiency, the above processes are generally carried out as recycle processes in which part of the gaseous effluent is recycled to the direct hydration reactor after recovery of the desired alcohol product. However, since ethane and propane are not affected in the direct hydration reaction, these components tend to build up in recycle hydration reaction systems, unless steps are taken to eliminate them from the system.

The removal of ethane or propane from a gas stream containing the corresponding alkene, i.e. ethene or propene, respectively, is complicated because of the difficulty of separating the alkene from the corresponding alkane. Fractional distillation is an effective method of separating these components. However, the alkene and corresponding alkane have volatility characteristics so similar that the cost of separating the alkene from the corresponding alkane by distillation is prohibitively high.

Due to the difficultly of separating ethene and propene from the corresponding alkanes, the buildup of ethane and propane in ethene and propene recycle gas processes, respectively, was usually prevented by purging part of the effluent from the system and combusting or otherwise disposing of the purged gas. The loss of valuable ethene and propene during the purge significantly detracts from the attractiveness of these processes.

The importance of recycle processes of the above type makes it desirable to continuously make efforts to enhance the efficiency of these processes. These efforts include investigations for improved method of separating ethene from ethane and propene from propane prior to recycling the ethene or propene to the reactor. The present invention provides such an improved method.

SUMMARY OF THE INVENTION

The present invention is a recycle process for producing ethanol and isopropanol which includes the steps of direct hydration of ethene or propene in the presence of a suitable catalyst, and separation of ethene from ethane or propene from propane by pressure swing adsorption or temperature swing adsorption.

According to a first embodiment of the invention, an alkene stream comprising ethene which contains ethane as an impurity or propene which contains propane as an impurity is contacted in a reaction zone with water in the presence of a direct hydration catalyst, thereby producing a gaseous product stream containing ethanol, when the alkene is ethene, or isopropanol, when the alkene is propene. The product stream also contains unreacted alkene and the corresponding alkane, and usually one or more hydration byproducts. The product stream leaving the hydration reactor is optionally cooled and then treated in a product recovery unit, such as a condenser or scrubber, to recover the alcohol. After recovery of the alcohol, the remaining alcohol-free gas stream is subjected to a pressure swing adsorption (PSA) process or a temperature swing adsorption (TSA) to recover unreacted alkene form the gas stream. Alternatively, part of the alcohol-free gas is subjected to the PSA process or TSA process and all or part of the remainder is recycled to the hydration reactor. The adsorption process is operated under conditions which result in the production of a non-adsorbed product stream containing most of the alkane contained in the product stream, and an adsorbed component containing most of the unreacted alkene. The process is desirably operated to retain substantially all of the unreacted alkene in the gas stream.

According to a second embodiment of the invention an alkene feed stream which contains the corresponding alkane as an impurity is first subjected to a PSA process or a TSA process. The adsorption process is desirably operated under the conditions specified above, so that an adsorbed stream enriched in the alkene and a non-adsorbed product stream enriched in the corresponding alkane are produced. The alkene-enriched gas stream obtained upon desorption of the adsorption beds is contacted with water in a reaction zone in the presence of an appropriate direct hydration catalyst under conditions which cause hydration of the alkene, thereby producing the product stream described above. The product stream is treated in the product recovery unit to recover substantially all of the product alcohol from the stream. As was the case in the first embodiment part or all of the alcohol-free gas stream remaining after the product recovery step can be recycled to the PSA or TSA process to recover the alkene from this stream; and, if only part is recycled to the PSA or TSA process, part or all of remainder can be recycled directly to the hydration reactor.

The adsorption step of either of the two above-described embodiments is typically carried out at a temperature in the range of about 0° C. to about 250° C., and is preferably carried out at a temperature above about 50° C. The adsorption step is generally carried out at an absolute pressure in the range of about 0.2 to 100 bar, and is preferably carried out carried out at an absolute pressure of about 1 to 50 bar.

In a preferred embodiment of the invention, the adsorbent is a type A zeolite, and in the most preferred embodiment, it is type 4A zeolite.

In other preferred embodiments of the invention the adsorption bed regeneration step is effected by vacuum means or by purging the bed with one or more of an inert gas, the non-adsorbed gas product from the adsorption system or the adsorbed product gas from the adsorption system, or by combinations of vacuum and purge regeneration; and bed repressurization is effected using the alkene-enriched desorbed gas from the adsorption system.

DETAILED DESCRIPTION OF THE INVENTION

Figure 1:
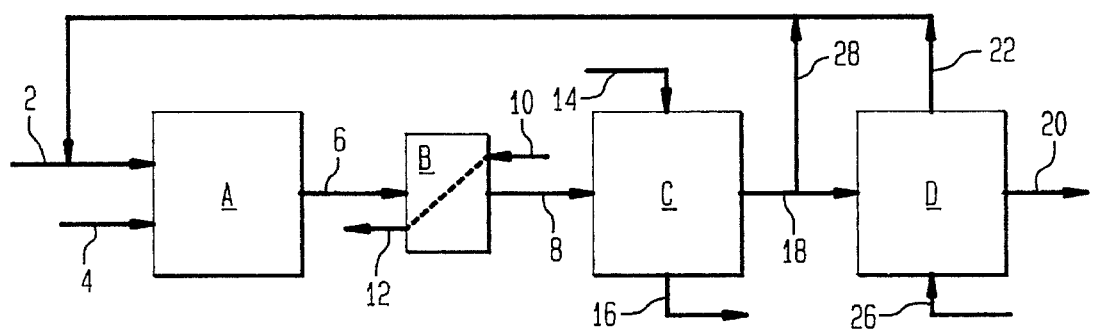
FIG. 1 illustrates, in a block diagram, one embodiment of a system for producing ethanol or isopropanol in accordance with the present invention.

As used in this specification, the term "alkene" means ethene or propene. When the alkene being referred to is ethene the "corresponding alkane" is ethane and when the alkene is propene the corresponding alkane is propane. The hydration can be conducted either in the liquid or gas phase. However, also in the interest of simplification of discussion, the invention will be described as it applies to vapor phase hydration.

In one aspect of the first embodiment of the invention an ethene feed stream containing ethane as an impurity is reacted with water in the vapor state in a reaction zone in the presence of a direct hydration catalyst, thereby producing ethanol. The conditions of the direct hydration reaction are well known and form no part of the invention. Typically, the hydration reaction is conducted at a temperature in the range of about 150° to about 300° C. and at pressures typically in the range of about 60 to about 80 bar, absolute. The reaction is conducted in the presence of a catalyst such as an acid such as, for example, phosphoric acid on a substrate such as glass beads, silica or silica-alumina. A gaseous reaction product comprising ethanol, some diethyl ether and acetaldehyde byproduct, unreacted ethene and water vapor, and ethane leaves the hydration reactor, is optionally cooled and then passed through a scrubber where it is washed with water to scrub the ethanol from the effluent stream. A caustic soda wash may also be included to neutralize any phosphoric acid carried out of the reactor with the product. The ethanol, together with water and diethyl ether byproduct, is removed from the scrubber as a liquid mixture and further treated to recover and purify the ethanol. The gaseous product exiting the scrubber is subjected to pressure swing adsorption or temperature swing adsorption to remove ethane from the gas stream and the ethene-rich stream from the adsorption zone is recycled to the hydration reactor.

In a second aspect of the first embodiment a propene feed stream containing propane as an impurity is reacted with water in the vapor state in a reaction zone in the presence of a direct hydration catalyst, such as an ion exchange resin, thereby producing isopropanol. Again, the conditions of the direct hydration reaction are well known and form no part of the invention. Typically, the hydration reaction is conducted at a temperature in the range of about 120° to about 200° C. and at pressures typically in the range of about 60 to about 100 bar. The isopropanol product and the propene- and propane-containing gas stream are separated and further treated in the manner described above.

The invention can be better understood from the accompanying drawings in which the same reference numerals are used to designate the same or similar pieces of equipment in different figures. Auxiliary equipment, including compressors, heat exchangers and valves, not necessary for an understanding of the invention, have been omitted from the drawings to simplify discussion of the invention.

The first embodiment is illustrated in FIG. 1, in which unit A is a direct hydration reactor, optional unit B is a heat exchanger, unit C is a product recovery unit and unit D is a gas separator.

Reactor A may be any suitable reactor and may be equipped with heat exchange means and an agitator (not shown). Reactor A is provided on its inlet end with alkene feed line 2 and water vapor inlet 4 and on its outlet end with gaseous effluent line 6, which is connected to the inlet of heat exchanger B, if this unit is included in the system, or to the inlet of product recovery unit D, if heat exchanger B is not used in the process.

In the embodiment illustrated in FIG. 1, heat exchanger B is provided with cooled gas outlet line 8 and with coolant inlet and outlet lines 10 and 12, respectively. Line 8 connects the cooled gas outlet end of heat exchanger B to the gas inlet end of product recovery unit C.

Product recovery unit C can be any unit suitable for separating the alcohol product from the gas components of the reactor effluent. Unit C is typically a condenser or a scrubber of the packed bed design equipped with means for spraying water or an aqueous or nonaqueous liquid on the product gas entering this unit from heat exchanger B (or from reactor A if the system does not include heat exchanger B). Unit C is equipped with scrubbing liquid inlet line 14 and liquid product discharge line 16. Unit C is also equipped with gas outlet line 18, which connects unit C to separator D.

The principal purpose of separator D is to separate ethene or propene from the gaseous effluent from product recovery unit C. Separator D is a pressure swing or temperature swing adsorption system typically comprising two or more stationary beds packed with the desired adsorbent. The beds are generally arranged in parallel and adapted to be operated in a cyclic process comprising adsorption and desorption. The cycle may contain steps other than the fundamental steps of adsorption and regeneration, and it is commonplace to have the system in which the adsorption is carried out comprise two or more adsorbent beds cycled out of phase to assure a pseudo-continuous flow of alkene-enriched gas from the outlet end of the adsorption system.

The adsorbent may be any adsorbent which selectively adsorbs alkenes from a gas mixture containing the alkenes and one or more alkanes. In general, the adsorbent may be alumina, silica, zeolites, carbon molecular sieves, etc. Typical adsorbents include alumina, silica gel, carbon molecular sieves, zeolites, such as type A and type X zeolite, etc. The preferred adsorbents are type A zeolites, and the most preferred adsorbent is type 4A zeolite.

Type 4A zeolite, i.e. the sodium form of type A zeolite, has an apparent pore size of about 3.6 to 4 Angstrom units. This adsorbent provides enhanced selectivity and capacity in adsorbing ethene from ethene-ethane mixtures and propene from propene-propane mixtures at elevated temperatures. This adsorbent is most effective for use in the invention when it is substantially unmodified, i.e. when it has only sodium ions as its exchangeable cations. However, certain properties of the adsorbent, such as thermal and light stability, may be improved by partly exchanging some of the sodium ions with other cations. Accordingly, it is within the scope of the preferred embodiment of the invention to use a type 4A zeolite in which some of the sodium ions attached to the adsorbent are replaced with other metal ions, provided that the percentage of ions exchanged is not so great that the adsorbent loses its type 4A character. Among the properties that define type 4A character are the ability of the adsorbent to selectively adsorb ethene from ethene-ethane mixtures and propene from propene-propane gas mixtures at elevated temperatures, and to accomplish this result without causing significant oligomerization or polymerization of the alkenes present in the mixtures. In general, it has been determined that up to about 25 percent (on an equivalent basis) of the sodium ions in 4A zeolite can be replaced by ion exchange with other cations without divesting the adsorbent of its type 4A character. Cations that may be ion exchanged with the 4A zeolite used in the alkene-alkane separation include, among others, potassium, calcium, magnesium, strontium, zinc, cobalt, silver, copper, manganese, cadmium, aluminum, cerium, etc. When exchanging other cations for sodium ions it is preferred that less than about 10 percent of the sodium ions (on an equivalent basis) be replaced with such other cations. The replacement of sodium ions may modify the properties of the adsorbent. For example, substituting some of the sodium ions with other cations may improve the stability of the adsorbent.

Another class of preferred adsorbents are those which contain certain oxidizable metal cations, such as copper-containing adsorbents, which possess enhanced adsorptive capacity and selectivity with respect to the preferential adsorption of alkenes from gaseous alkene-alkane mixtures. Suitable adsorbent substrates for manufacturing copper-modified adsorbents include silica gel, and zeolite molecular sieves, such as zeolite type 4A, zeolite type 5A, zeolite type X and zeolite type Y. The manufacture and use of copper-modified adsorbents and examples of suitable copper-containing adsorbents are set forth in U.S. Pat. No. 4,917,711, the disclosure of which is incorporated herein by reference.

Separator D is provided with waste gas discharge line 20, alkene recycle line 22, which connects the desorbed product outlet of separator D with the inlet of hydration reactor A, and purge gas inlet line 26. Recycle line 28 connects line 18 to recycle line 22.

According to the process of the invention practiced in the system of FIG. 1, an alkene feed stream, which may be an ethene stream which contains ethane as an impurity or a propene stream which contains propane as an impurity, and water vapor are heated to the desired hydration reaction temperature and introduced into reactor A through lines 2 and 4, respectively. Alternatively, the alkene and water vapor streams may be combined and introduced into reactor A in a single line. The alkene feed stream usually contains at least 90% by volume of the desired alkene reactant, with the balance being the corresponding alkane, and in preferred embodiments the concentration of alkene in the feed entering reactor A is at least about 95%.

In reactor A, the gas mixture contacts the catalyst at the conventional conditions of temperature and pressure mentioned above and reacts to form the alcohol product. A hot gaseous effluent is discharged from reactor A through line 6. In the embodiment illustrated in FIG. 1, the hot effluent enters heat exchanger B and is cooled therein by indirect heat exchange with a coolant, such as water. During the cooling some of the higher boiling components of the product stream may condense. The condensed product can be separated from the gas effluent in heat exchanger B through a condensate discharge line (not shown) and later combined with the liquid product recovered in product recovery unit C, or if desired, all of the partially condensed gas mixture can be sent to product recovery unit C for separation from the gaseous components of the reactor effluent. As noted above, heat exchanger B may not be included in the system. In such case the hot gaseous effluent from reactor A is sent directly to unit C for product recovery.

The product stream from unit B (or from reactor A, if the system does not include unit B) next enters product recovery unit C, which, for purposes of description will be considered to be a gas scrubber. The product gases entering unit C are intimately contacted with a solvent for the alcohol. The solvent, which is usually water, dissolves substantially all of the alcohol and higher boiling byproducts in the product gas stream. The product-containing solution exits scrubber C via line 16 and is transported to downstream treatment units for recovery and purification of the alcohol. The scrubbed gas stream leaves product recovery unit C through line 18 and part or all of this stream is next sent to separator D. When only part of this stream is sent to separator D, the remainder is recycled to reactor A through lines 28 and 22 or removed from the system through a waste stream discharge line (not shown).

Separator D is preferably operated in a manner which results in the adsorption of substantially all of the alkene in the feed stream to this unit. During the adsorption step most of the alkane present is separated from the feed gas and discharged from the system as non-adsorbed gas through line 20.

The temperature at which the adsorption step is carried out depends upon a number of factors, such as the particular adsorbent being used, e.g. unmodified 4A zeolite, a particular metal-exchanged 4A zeolite or another adsorbent which selectively adsorbs alkenes from alkene-alkane mixtures, and the pressure at which the adsorption is carried out. In general, the adsorption step is carried out at a minimum temperature of about 0° C. and is preferably carried out at a minimum temperature of about 50° C. and is most preferably carried out at a temperature of at least about 70° C. The upper temperature limit at which the adsorption step in unit A is carried out is determined mostly by economics. In general the adsorption step can be carried out at a temperature below the temperature at which the alkene undergoes chemical reaction, such as polymerization. The upper adsorption temperature limit is about 250° C. When unmodified 4A zeolite is used as the adsorbent the reaction is generally carried out at or below 200° C., and is preferably carried out at a temperature at or below 170° C. Oxidizable metal-containing adsorbents, such as copper modified adsorbents, are particularly effective at temperatures above about 100° C., for example at temperatures between about 100° C. and 250° C. They are preferably used at temperatures in the range of about 110° to 200° C., and most preferably at temperatures in the range of about 125° to about 175° C.

The pressures at which the adsorption and regeneration steps of the adsorption process are carried out are not critical, and in general these steps can be carried out at pressures which are congruous with the operating conditions of the hydration process, with the limitation, of course, that the adsorption step be carried out at a pressure greater than the regeneration step pressure. Typically, when the adsorption process is pressure swing adsorption the absolute pressure during the adsorption step will range generally from about 0.2 to about 100 bar, and preferably from about 1 to 50 bar, and during the regeneration step will range from about 20 millibar to about 1 bar or more. When the adsorption process is temperature swing adsorption the pressure during both adsorption and desorption is desirably atmospheric or near atmospheric.

When the adsorbed alkene front traveling through the vessel(s) of separator D in which the adsorption step is being carried out reaches the desired point in the vessel(s), the adsorption process in these vessel(s) is terminated and these vessels enter the regeneration mode. During regeneration, the alkene-loaded vessels are depressurized, if the adsorption cycle is pressure swing adsorption, or heated, if a temperature swing adsorption cycle is employed. As the regeneration proceeds alkene-enriched gas is discharged from separator D through line 22 and returned to reactor through line 22.

The method of regeneration of the adsorption beds depends upon the type of adsorption process employed. In the case of pressure swing adsorption, the regeneration phase generally includes a countercurrent depressurization step during which the beds are vented countercurrently until they attain the desired lower pressure. Alternatively, they may be evacuated to subatmospheric pressure by means of a vacuum inducing device, such as a vacuum pump (not shown). In either case the alkene desorbed from the beds is recycled to reactor A via line 22.

In some cases, in addition to the countercurrent depressurization step(s), it may be desirable to purge the bed with an inert gas or one of the gas streams exiting separator D. In this event the purge step is usually initiated towards the end of the countercurrent depressurization step, or subsequent thereto. During the purge step, a nonadsorbable purge gas is introduced into separator D via line 26 and passed countercurrently through the adsorbent beds, thereby forcing desorbed alkene out of separator D and through line 22. The purge gas may be nonadsorbed product gas exiting separator D through line 20 or a nonadsorbable gas obtained from a different source, such as an inert permanent gas like nitrogen.

In a preferred method of operation of the system of FIG. 1, the alkene desorbed from separator D during the countercurrent depressurization step(s) is recycled to reactor A through line 22, and all or a portion of the purge gas and alkene desorbed from the bed during the purge step is recycled to separator D for reprocessing through the adsorption system. The advantage of this embodiment is that it permits the amount of purge gas that is recycled to reactor A to be minimized.

The adsorption cycle may contain steps other than the fundamental steps of adsorption and regeneration. For example, it may be advantageous to depressurize the adsorption bed in multiple steps, with the first depressurization product being used to partially pressurize another bed in the adsorption system. This will further reduce the amount of gaseous impurities recycled to reactor A. It may also be desirable to include a cocurrent purge step between the adsorption phase and the regeneration phase. The cocurrent purge is effected by terminating the flow of feed gas into separator D and passing high purity alkene cocurrently into the adsorption bed at adsorption pressure. This has the effect of forcing nonadsorbed gas in the void spaces in separator D toward the nonadsorbed gas outlet, thereby ensuring that the alkene produced during the countercurrent depressurization will be of high purity. The high purity alkene used for the cocurrent purge can be obtained from an intermediate storage facility in line 22 (not shown), when separator D comprises a single adsorber; or from another adsorber that is in the adsorption phase, when separator D comprises multiple adsorbers arranged in parallel and operated out of phase, or from alkene feed line 2.

Figure 2:
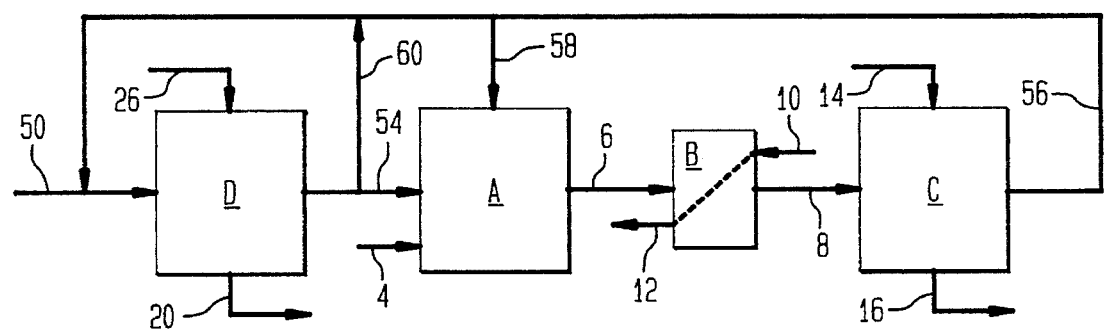
FIG. 2 illustrates, in a block diagram, an alternate embodiment of the system illustrated in FIG. 1.

The system illustrated in FIG. 2 is a variation of the system of FIG. 1. Units A, B, C and D of FIG. 2 are identical to the corresponding units of FIG. 1, except that separator D of FIG. 2 may be larger than separator D of FIG. 1. The principal difference between the system of FIGS. 1 and 2 is that in the FIG. 2 system separator D is positioned upstream of reactor A. As was the case with the FIG. 1 system, heat exchanger B is optional in the system of FIG. 2.

In practicing the process of the invention in the system of FIG. 2, a feed stream comprised substantially of alkene, but containing the corresponding alkane as an impurity, is introduced into separator D through line 50. The feed stream is subjected to pressure swing adsorption or temperature swing adsorption in separator D, as described above. Nonadsorbed alkane-enriched product is discharged from separator D through line 20 and desorbed alkene-enriched product is recovered from unit D through line 54. The alkene-enriched product next enters reactor A wherein the alkene reacts with the water vapor entering reactor A through line 4 to form the desired alcohol under the conditions set forth above. The reaction product is discharged from reactor A through line 6 and it next enters heat exchanger B, if this unit is included in the system. The product is cooled in unit B, as described above, and forwarded to scrubber C through line 8. The alcohol-containing liquid product is scrubbed from the product stream in scrubber C and removed therefrom through line 16 and is discharged from the system for further treatment or purification. The alkene-rich gas stream leaves scrubber C through line 56, and all of it can be recycled to separator D or part can be recycled to separator D and the remainder recycled to reactor A through line 58.

As was the case in operating the FIG. 1 system, when the regeneration of separator D is conducted with both countercurrent depressurization step(s) and a purge step, it is preferred to send all of the alkene desorbed during the countercurrent depressurization step(s) to reactor A and recycle part or all of the purge gas and alkene desorbed from the bed during the purge step to separator D through lines 60 and 56 for reprocessing in the adsorption system.

It will be appreciated that it is within the scope of the present invention to utilize conventional equipment to monitor and automatically regulate the flow of gases within the system so that it can be fully automated to run continuously in an efficient manner.

An important advantage of the invention is that it permits operation of the process of this invention at a relatively low per pass conversion of the alkene feed to achieve substantially improved selectivity to the desired alcohol product. It will be appreciated that a system that achieves enhanced selectivity, and hence increased overall yield of a desired product, is highly beneficial.

The invention is further illustrated by the following example in which, unless otherwise indicated, parts, percentages and ratios are on a volume basis. The following example illustrates the process of the invention as it applies to the direct hydration of ethene to produce ethanol using as feed an ethene gas stream containing ethane as an impurity, but the scope of the invention is to be construed as also including the direct hydration of propene to produce isopropanol.

EXAMPLE I

This hypothetical example depicts a vapor phase ethanol production run using as feed components ethene containing 99.9% ethene and 0.1% ethane and water. The example is simulated for practice in a reaction system similar to the system of FIG. 1, comprising a hydration reactor, a water scrubbing unit and a pressure swing adsorption unit containing a bed of type 4A zeolite. The simulated hydration reaction is carried out at a temperature of −250° C. and a pressure of 70 bar. The simulated adsorption process is carried out at an adsorption temperature and pressure of 250° C. and 3 bar, absolute, respectively, and bed regeneration to a pressure of 300 millibar.

The stream flows and compositions are tabulated in the Table. In the table, stream (1) is the fresh feed into the reaction system; stream (2) is the feed to the hydration reactor; stream (3) is the effluent stream from the reactor; stream (4) is the flow of scrubbed ethanol stream from the scrubber; stream (5) is the flow of gaseous effluent from the scrubber; stream (6) is the portion of stream (5) that is recycled directly to the hydration reactor; stream (7) is the portion of stream (5) that is sent to the pressure swing adsorption system; stream (8) is the flow of recycle to the hydration reactor; and stream 9 is the flow of waste gas from the pressure swing adsorption system. Stream (2) is combined flows of streams (1), (6) and (8).

TABLE 1

| | | Stream | | | | | | | | |
|---|---|---|---|---|---|---|---|---|---|---|
| Component | Sel | 1 mole | 2 mole | 3 mole | 4 mole | 5 mole | 6 mole | 7 mole | 8 mole | 9 mole |
| Ethene | | 107.568 | 1834.324 | 1731.602 | 3.117 | 1728.485 | 1711.200 | 17.284 | 15.556 | 1.728 |
| Ethane | | 0.108 | 11.975 | 11.975 | 0.012 | 11.963 | 11.843 | 0.120 | 0.024 | 0.096 |
| Ethanol | 0.974 | | | 100.000 | 100.000 | 0.000 | 0.000 | 0.000 | 0.000 | 0.000 |
| Water | | 950.201 | 955.377 | 855.377 | 850.159 | 5.218 | 5.166 | 0.052 | 0.010 | 0.042 |
| Acetaldehyde | 0.003 | 0.000 | 0.000 | 0.257 | 0.257 | 0.000 | 0.000 | 0.000 | 0.000 | 0.000 |
| Diethyl Ether | 0.024 | | | 2.465 | 2.465 | 0.000 | 0.000 | 0.000 | 0.000 | 0.000 |
| Total | 1.000 | 1057.876 | 2801.675 | 2701.675 | 956.010 | 1745.665 | 1728.209 | 17.456 | 15.591 | 1.866 |

Although the invention has been described with particular reference to a specific system, the described system is merely exemplary of the invention and variations are contemplated. For example, other catalysts can be used in the invention, if desired. Similarly, the process of the invention may be practiced in equipment arrangements other than those illustrated in the drawings. The scope of the invention is limited only by the breadth of the appended claims.

We claim:

1. A process for the production of ethanol comprising the steps:
   (a) contacting an ethene-ethane mixture and water with a hydration catalyst in a reaction zone under conditions which result in the production of a gaseous product containing ethanol, unreacted ethene and ethane;
   (b) recovering said ethanol from said gaseous product;
   (c) selectively adsorbing ethene from the substantially ethanol-free gaseous product by passing at least part of the substantially ethanol-free gaseous product through an adsorption zone containing 4A zeolite adsorbent at a temperature above about 50° C.;
   (d) regenerating said adsorbent, thereby producing an ethene-enriched gas stream; and
   (e) recycling said ethene-enriched gas stream to said reaction zone.

2. A process for the production of ethanol comprising the steps:
   (a) selectively adsorbing ethene from a ethene-ethane gas mixture by passing said gas mixture through an adsorption zone containing 4A zeolite adsorbent at a temperature above about 50° C.;
   (b) regenerating said adsorbent, thereby producing ethene-enriched gas;
   (c) contacting said ethene-enriched gas with water vapor in the presence of a hydration catalyst in a reaction zone under conditions which result in the production of a gaseous product containing ethanol, unreacted ethene and ethane;
   (d) recovering the ethanol from said gaseous product; and
   (e) recycling part or all of the substantially ethanol-free gaseous product to said adsorption zone.

3. A process for the production of isopropanol comprising the steps:
   (a) contacting a propene-propane mixture and water with a hydration catalyst in a reaction zone under conditions which result in the production of a gaseous product containing isopropanol, unreacted propene and propane;
   (b) recovering said isopropanol from said gaseous product;
   (c) selectively adsorbing propene from the substantially isopropanol-free gaseous product by passing at least part of the substantially isopropanol-free gaseous product through an adsorption zone containing 4A zeolite adsorbent at a temperature above about 50° C.;
   (d) regenerating said adsorbent, thereby producing a propene-enriched gas stream; and
   (e) recycling said propene-enriched gas stream to said reaction zone.

4. A process for the production of isopropanol comprising the steps:
   (a) selectively adsorbing propene from a propene-propane gas mixture by passing said gas mixture through 4A zeolite adsorbent at a temperature above about 50° C.;
   (b) regenerating said adsorbent, thereby producing propene-enriched gas;
   (c) contacting said propene-enriched gas with water vapor in the presence of a hydration catalyst in a reaction zone under conditions which result in the production of a gaseous product containing isopropanol, unreacted propene and propane;
   (d) recovering the isopropanol from said gaseous product; and
   (e) recycling part or all of the substantially isopropanol-free gaseous product to said adsorption zone.

5. The process of claim 1, 2, 3 or 4, wherein the adsorption step is conducted at a temperature in the range of about 50° to about 250° C.

6. The process of claim 5, wherein the adsorbent contains an oxidizable metal ion.

7. The process of claim 6, wherein said oxidizable metal ion is copper ion.

8. The process of claim 7, wherein the adsorption step is carried out at a temperature between about 100° and about 200° C.

9. The process of claim 5, wherein said adsorbent contains exchangeable cations other than sodium ions, but at a level insufficient to divest the adsorbent of its 4A character.

10. The process of claim 1, 2, 3 or 4, wherein the adsorption step is carried out at a temperature in the range of about 50° to about 200° C. and an absolute pressure in the range of about 0.2 to about 100 bar.

11. The process of claim 5, wherein the adsorption step is carried out at a temperature in the range of about 70° to about 170° C. and an absolute pressure of about 1 to 50 bar.

12. The process of claim 1, 2, 3 or 4, wherein the adsorption and regeneration steps comprise a pressure swing adsorption cycle.

13. The process of claim 12, wherein the adsorbent is at least partly regenerated by countercurrent depressurization.

14. The process of claim 13, wherein the adsorbent is further regenerated by depressurization to subatmospheric pressure by means of vacuum.

15. The process of claim 13, wherein the adsorbent is further regenerated by purging the bed with an inert gas, the nonadsorbed product gas, the desorbed product gas or combinations of these.

* * * * *